United States Patent [19]

Müller et al.

[11] Patent Number: 4,530,115

[45] Date of Patent: Jul. 23, 1985

[54] SHANK FOR A PROSTHESIS

[75] Inventors: Maurice E. Müller, Bern; Peter G. Niederer, Zollikofen; Otto Frey, Winterthur, all of Switzerland

[73] Assignees: Gebrüder Selzer AG, Winterthur; Protek AG, Bern, both of Switzerland

[21] Appl. No.: 454,991

[22] Filed: Jan. 3, 1983

[30] Foreign Application Priority Data

Jan. 29, 1982 [CH] Switzerland .................... 541/82

[51] Int. Cl.³ .......................... A61F 1/04; A61F 5/04
[52] U.S. Cl. ................................. 623/23; 128/92 C; 128/92 BC; 623/18
[58] Field of Search ............... 3/1.9, 1.81, 1.911, 3/1.512, 1.513; 128/92 C, 92 CA, 92 B, 92 BA, 92 BB, 92 BC, 92 D, 92 E

[56] References Cited

U.S. PATENT DOCUMENTS 2,486,303  11/1949  Longfellow ................. 128/92 B

FOREIGN PATENT DOCUMENTS

| 560587 | 9/1957 | Belgium | 128/92 BC |
| 2519488 | 11/1976 | Fed. Rep. of Germany | 128/92 BC |
| 893401 | 6/1944 | France | 128/92 BC |
| 1278359 | 10/1961 | France | 128/92 CA |

Primary Examiner—Richard J. Apley
Assistant Examiner—David Isabella
Attorney, Agent, or Firm—Kenyon & Kenyon

[57] ABSTRACT

The prosthesis shank is composed of a blade which carries a joint head and a wedge-shaped end piece. The end piece is driven in along a guide in the lateral narrow side of the blade while the blade remains in a fixed position. The wedge-shaped form of the end piece permits fixation of the blade at a predetermined height such that the joint head can be at the level of the trochanter tip.

17 Claims, 6 Drawing Figures

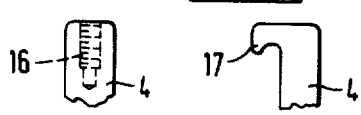
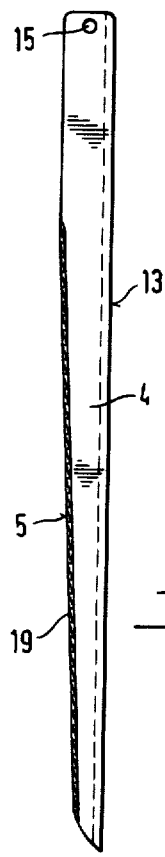
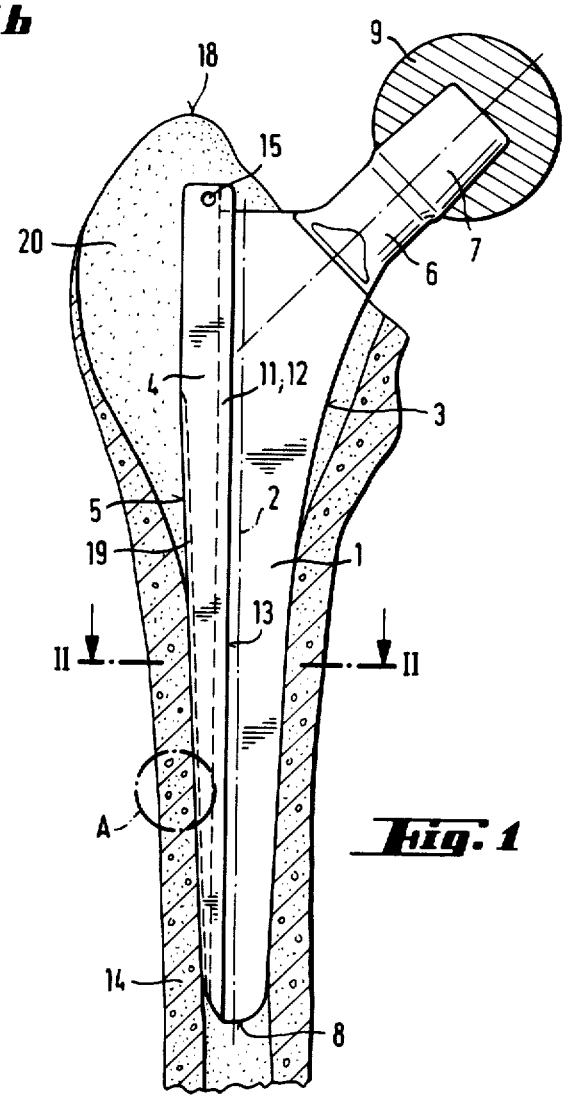
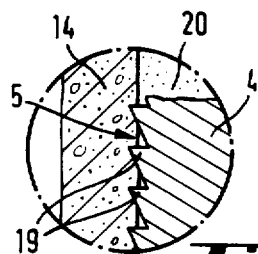
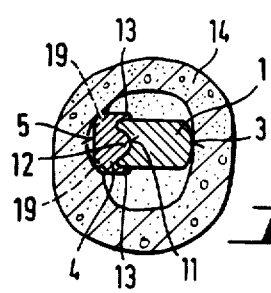

SHANK FOR A PROSTHESIS

This invention relates to a shank for a prosthesis. More particularly, this invention relates to a straight blade-type shank for a joint endoprosthesis.

Heretofore, various types of prosthesis shanks have been known for the anchoring of a bone implant, for example for a hip joint prosthesis. In some cases, for example, as described in Swiss Pat. No. 622,423, the shanks have been constructed in a straight blade-type manner. In these cases, the sides of the blade first widen conically from the distal end symmetrically to a longitudinal median axis with the conical taper along a lateral narrow side ending at about three quarters of the shank height. Thereafter, the medial side of the blade extends in a steadily curved bend into a prosthesis neck on which a joint head can be mounted.

Generally, these known shanks are utilized for a cement-free or, at least a cement-poor, anchoring of the prosthesis in a bone. In the case of a cement-poor anchoring, the bone cement acts as a filling material and is relieved of a load-bearing function. Further, the bearing support in this type of anchoring system is effected to a large extend by a wedging of the shank in the bone.

As is known, in order to insure a functionally correct position of a joint head of a prosthesis, the prosthesis must be implanted so that the center of the joint head is located approximately at the level of the tip of the greater trochanter. However, in many cases, if the shank is fixed mainly by wedging, it is very often difficult for an operating surgeon to comply with this requirement.

Accordingly, it is an object of the invention to facilitate the fixing of a joint head of a prosthesis at a certain level.

It is another object of the invention to provide a shank for a prosthesis which can be accurately positioned during implantation.

It is another object of the invention to provide a shank for a prosthesis which permits subsequent adjustments to be made.

Briefly, the invention provides a shank for a prosthesis which is comprised of a blade and a wedge-shaped lateral end piece. The blade is formed with a conically widening shape which extends from a distal end along a longitudinal median axis and a guide which extends along one narrow lateral side to slidably receive the end piece. In addition, the blade includes a neck at a proximal end, for example for receiving a joint head for a hip joint prosthesis.

With this prosthesis, the blade which carries the joint head can first be driven into a prepared bone and retained in a position in which the joint head is at a specified level relative to the greater trochanter. Thereafter, the end piece can be slipped onto the guide of the blade and can be driven into place while the blade is being retained. During this time, the wedge form of the end piece causes a wedging of the entire shank in the bone without changing the level position of the joint head and shank blade, respectively.

Another advantage of the prosthesis is that a series of different shank widths can be provided by one or two shank blades and a plurality of end pieces of different widths. Such a series can be prepared much more economically than in the case where a separate shank for each shank width of a set is provided.

Furthermore, minor corrections, for example, if the shank has loosened, may be possible at a later time after implantation at no greater expense. In this case, the end piece can be hammered in a further distance in a minor operation, again, with the blade being retained in place.

The hammering in of the wedge-shaped end piece is facilitated if the guide on the blade runs parallel to the longitudinal median axis of the shank. In addition, in order to improve the fixation of the end piece in a bone, the end piece can be provided with barb-type serrations on an outer surface, i.e. along the conical expansion of the piece. The serrations may advantageously be arranged in two corners of the end piece along the lateral narrow side thereof.

In order to impede growth of tissue into the guide from above at the proximal end of the shank, the lateral narrow side of the end piece extends in parallel to the longitudinal median axis in the upper proximal region of the shank height. This also has the advantage of improving the transmission of rotation forces from the trochanger to the implant and vice versa.

In order to facilitate extraction of the end piece in the case of a re-operation, a means may be provided at one end for engaging with an extraction tool.

The guide on the blade may be shaped relative to the end pieces so that the end piece and blade engage over one another so as to prevent lateral sliding off of the end piece from the lateral narrow side of the blade. In addition, in order to further ensure a mutual adhesion of the blade and end piece, the friction surface should be made as large as possible. Moreover, as is customary in implant technology, the guide may have a rounded form so as to avoid load peaks in the implant or bone.

The blade and end piece may be made primarily of metals and metal alloys which are commonly used in implant technology. However, both parts may also be made of a ceramic material or a plastic and both may be provided with suitable coatings. In order to avoid a cold welding of the guide surfaces of the blade and end piece during insertion of the end piece, each is advantageously made of different metals which do not tend to cold weld. For example, the blade and end piece may be made of titanium or a cobalt-based alloy. Another possibility is to provide one or both guide surfaces with a suitable hard layer, for example of TiN, for the same purpose.

These and other objects and advantages will become more apparent from the following detailed description taken in conjunction with the accompanying drawings wherein:

FIG. 1 illustrates a longitudinal section through the upper end of a femur bone having a hip joint prosthesis fixed therein with a shank in accordance with the invention;

FIG. 2. illustrates a view taken on line II—II of FIG. 1;

FIG. 3 illustrates an enlarged detailed view taken at the section A of FIG. 1;

FIG. 4 illustrates a side view of an end piece in accordance with the invention; and FIGS. 5a and 5b illustrate the upper ends of an end piece having a means for engaging with an extraction tool.

Referring to FIG. 1, the blade type prosthesis shank is constructed to expand conically on all sides from the distal end 8. The shank is composed of a blade 1 proper and a wedge-shaped end piece 4 which is abutted against the lateral narrow side of the blade 1 while extending over the entire shank length as shown. As indicated, the shank has a conical widening shape which extends from the distal end 8 symmetrically along a longitudinal median axis 2. In addition, the median narrow side 3 of the blade 1 changes over into a curve or arc which extends to a neck 6. In known manner, the neck 6 extends to a pin or peg 7 which is conically tapered to receive a spherical joint head 9 in known manner. The axis of the pin 7 intersects with the longitudinal median axis 2 of the shank at an angle which essentially corresponds to the angle between the shank neck 6 (at the proximal end) and the femur axis of a natural hip joint. In the present case, this angle is 45°.

The end piece 4 has a wedge shape in the longitudinal direction as indicated in FIG. 4.

The blade 1 also has a guide extending along the lateral narrow side for slidably receiving the end piece 4. This guide consists of a fillet 11 in the lateral narrow side which is rounded on all sides. In a similar manner, the end piece 4 has a projecting longitudinal rib or ridge 12 which mates within the fillet 11. In addition, the end piece has two edges 13 which overlap the blade 1 so as to overlap the side flanks of the fillet 11. In this way, the end piece 4 is prevented from sliding off the shank blade 1 laterally.

In order to prevent cold welding, the blade 1 and the end piece 4 are made of different materials. For example, the blade 1 consists of a chromium based alloy while the end piece 4 is made of titanium. Alternatively, the end piece 4 may be covered with a titanium base hard layer at least along the guide.

As indicated in FIG. 1, the expansion of the conical taper of the shank continues to about ⅝ to ¾ of the shank height on the lateral narrow side 5. Thereafter, the lateral narrow side 5 of the end piece 4 extends parallel to the longitudinal median axis 2.

Referring to FIGS. 2 and 3, the end piece 4 is provided with a plurality of barb-type serrations on the outer surface, i.e. at the corners along the lateral narrow side 5. The serrations 19 are shaped as indicated in FIG. 3 so as to permit insertion into a cortical bone substance 14 while thereafter preventing an unintentional extraction of the wedge-shaped end piece 4.

As indicated in FIG. 2, the end piece 4 is of a greater thickness than the blade 1.

Referring to FIG. 4, the end piece 4 may also be provided with a means in the form of an eyelet 15 at the upper or proximal end for engaging with an extraction tool. Alternatively, as indicated in FIG. 5a, the means may be in the form of a suitable coupling element such as a thread 16 or, as indicated in FIG. 5b, in the form of a hook type projection 17.

In use, the blade 1 of the shank may be provided with a joint head 9 and thereafter fitted into a surgically prepared spongious bone tissue 20 far enough for the center of the joint head 9 to be located approximately at the level of the trochanter tip 18 of the femur bone. Thereafter, with the blade 1 and joint head 9 retained in place, the end piece 4 may be inserted. This may be carried out, for example, by using a hammering tool. Blade 1 and end pieces 4 thus become mutually wedged together between opposite regions of the cortical bone substance 14.

The invention thus provides a multi-piece shank for a prosthesis which permits an accurate placement of a joint head for a hip joint prosthesis. Further, the multi-piece construction of the shank permits the work of the operating surgeon to be greatly facilitated.

The invention further provides a multi-piece shank which can be "tightened" from time to time should any looseness in the implanted prosthesis occur.

What is claimed is:

1. A shank for a prosthesis comprising
    a blade having a conically widening shape extending from a distal end to a proximal end along a longitudinal median axis, said blade including a neck at said proximal end and a guide extending along one lateral narrow side thereof; and
    a lateral end piece having a wedge shape in the longitudinal direction slidably received in said guide and extending over the entire length of the shank.

2. A shank as set forth in claim 1 wherein a narrow lateral side of said end piece widens from said distal end to about ¾ of the length of said shank and an opposite narrow medial side of said blade extends on a curve into said neck.

3. A shank as set forth in claim 1 wherein said guide extends in parallel to said median axis.

4. A shank as set forth in claim 3 wherein said end piece has a plurality of barb-type serrations on an outer surface.

5. A shank as set forth in claim 1 wherein said end piece has a plurality of barb-type serrations on an outer surface.

6. A shank as set forth in claim 5 wherein said serrations are arranged in two corners of said end piece along a lateral narrow side thereof.

7. A shank as set forth in claim 1 wherein said end piece has a lateral narrow side in its upper proximal region parallel to said median axis.

8. A shank as set forth in claim 1 wherein said end piece includes means at one end for engaging with an extraction tool.

9. A multi-piece shank for a prosthesis comprising
    a blade of concically widening shape extending from a distal end to a proximal end along a longitudinal median axis, said blade having a guide extending along a lateral narrow side thereof; and
    an elongated end piece slidably received in said guide and extending from said distal end, said end piece having a wedge shape in the longitudinal direction.

10. A multi-piece shank as set forth in claim 9 wherein said end piece has a plurality of barb-type serrations of an outer surface.

11. A multi-piece shank as set forth in claim 10 wherein said end piece means at one end for engaging with an extraction tool.

12. A multi-piece shank as set forth in claim 9 wherein said end piece has a lateral narrow side parallel to said median axis in an upper proximal region of said blade.

13. A multi-piece shank as set forth in claim 9 wherein said end piece is of greater thickness than said blade.

14. A multi-piece shank as set forth in claim 13 wherein said end piece includes means at one end for engaging with an extraction tool.

15. A multi-piece shank as set forth in claim 9 wherein said end piece has an elongated rib slidably received in said guide and a pair of longitudinal edges overlapping said blade to retain said end piece laterally of said blade.

16. A multi-piece shank as set forth in claim 9 wherein said blade includes a neck extending at an angle to said median axis to receive a joint head thereon.

17. A method of implanting a joint head of a prosthesis comprising the steps of
    fitting a blade having a conically widening shape along a longitudinal median axis, a neck at a proximal end to receive a joint head and a guide along a lateral narrow side within a surgically prepared spongious bone tissue of a bone;

locating the center of the joint head at a predetermined point relative to the bone; and thereafter inserting an elongated wedge-shaped end piece into and along said guide to wedge the end piece and blade together within the bone tissue while retaining the blade with said center at said predetermined point.

* * * * *